United States Patent [19]

Ellis et al.

[11] Patent Number: 5,397,308
[45] Date of Patent: Mar. 14, 1995

[54] BALLOON INFLATION MEASUREMENT APPARATUS

[75] Inventors: Louis Ellis, St. Anthony; Roger N. Hastings, Burnsville; Ling Shang, Maple Grove, all of Minn.

[73] Assignee: SciMed Life Systems, Inc., Maple Grove, Minn.

[21] Appl. No.: 142,498

[22] Filed: Oct. 22, 1993

[51] Int. Cl.⁶ .................... A61M 25/00; A61M 29/00
[52] U.S. Cl. ..................... 604/100; 606/192
[58] Field of Search .......... 604/20, 21, 96–100; 128/642, 734, 748; 606/192–196; 73/861.08

[56] References Cited

U.S. PATENT DOCUMENTS

| | | | |
|---|---|---|---|
| 1,734,084 | 11/1929 | Funck | 128/734 X |
| 3,649,948 | 3/1972 | Porter | 128/748 X |
| 3,661,148 | 4/1972 | Kolin . | |
| 3,686,958 | 8/1972 | Porter et al. | 128/748 X |
| 3,789,667 | 2/1974 | Porter et al. | 128/748 X |
| 4,587,975 | 5/1986 | Salo et al. | 128/693 |
| 4,593,703 | 6/1986 | Cosman | 128/748 |
| 4,651,738 | 3/1987 | Demer et al. . | |
| 4,738,267 | 4/1988 | Lazorthes et al. | 128/748 |
| 4,836,214 | 6/1989 | Sramek | 128/693 |
| 4,901,735 | 2/1990 | von Berg | 128/748 |
| 4,924,877 | 5/1990 | Brooks | 128/748 |
| 5,129,396 | 7/1992 | Rosen et al. | 128/653.1 |
| 5,135,001 | 8/1992 | Sinofsky et al. | 128/662.06 |
| 5,171,299 | 12/1992 | Heitzmann et al. | 604/100 |

OTHER PUBLICATIONS

*Fundamentals of Physics*, Halliday, D. et al. (John Wiley & Sons, New York, 1981), pp. 506–508.

Zebley et al., *Catheter-Tip technique for Continuous Measurement of the Internal Cross-Sectional Area of Blood Vessels*, 25th ACEMB, Oct. 1972, p. 143.

Holtz et al., *Phasic Registration of Venous Diameter Changes in-situ with the Induction Angiometer*, Pfugers Archiv. 377 (1978), pp. 177–180.

*Primary Examiner*—John D. Yasko
*Assistant Examiner*—Adam J. Cermak
*Attorney, Agent, or Firm*—Nawrocki, Rooney & Sivertson

[57] ABSTRACT

An improved balloon catheter for angioplasty and the like for measuring the inflation of a balloon after insertion into the body. A pair of electrodes are mounted in spaced relation within the balloon interior wall such that as the internal area within the balloon is varied by inflation of the balloon with an electrically conductive fluid, the electrodes monitor the changing electrical resistance between the electrodes. The electrodes are connected through the catheter to an external electrical measurement circuit for measuring the change in resistance and thus determining the amount of balloon inflation.

19 Claims, 4 Drawing Sheets

BALLOON INFLATION MEASUREMENT APPARATUS

BACKGROUND OF THE INVENTION

1. Field of the Invention

The present invention generally relates to the field of intravascular medicine and more particularly to the field of catheters, and still more particularly to balloon catheters such as dilation catheters used for medical treatments within the body.

2. Description of the Prior Art

The use of intravascular catheters for treatment of the body is well known in the field of medicine. The use of dilation or balloon catheters has become widespread in the treatment, for example, of restrictions within the coronary blood vessels, such as stenotic lesions. In this balloon angioplasty, a catheter carrying a balloon at its distal end is guided through the blood vessel to a point adjacent the lesion. The placement of the balloon is aided by use of a fluoroscope and radiopaque elements, as well as other modern technological advances. The size and type of the balloon is generally selected by the physician based on his knowledge of the size and type of lesion. The balloon is then expanded by providing an expansion fluid from the proximal end of the catheter through a fluid lumen within the catheter to the balloon. The expanded balloon acts on the lesion in a manner to reopen at least a portion of the restricted vessel. The balloon is then deflated for removal from the body, though sometimes repeated reinflation may be deemed necessary by the physician prior to removal.

Though balloon angioplasty is well known as a safe and effective method for treatment of the vascular disease described above, there are still problems that arise during the procedure. For example, stenotic lesions often have a highly irregular cross-sectional configuration, and may vary greatly in their hardness, both of which make for difficulty in determining what size and composition of balloon to use, and how often to inflate it.

It is known in the field that if the physician can have information as to the amount of inflation the fluid has caused in the balloon under use, he can use this knowledge to increase the chance of completing a successful angioplasty while at the same time having less risk of damage to the vessel which could be caused by over-inflation or repeated reinflation of the balloon. A known way of providing the desired balloon inflation size is to monitor the pressure within the balloon during the inflation procedure, transform the measured pressure into electrical signals, conduct the signals from the body to a microcomputer outside the catheter, and provide the physician with inflation information based on the known and previously charted relationship between pressure and the inflation of the type of balloon being used.

One example of this prior art solution to the problem is shown in U.S. Pat. No. 5,171,299, issued Dec. 15, 1992 to H. A. Heitzmann et al. One of the difficulties with this solution for the problem at hand is that it is necessary to place a pressure transducer within the catheter and in contact with the interior of the balloon. Such a transducer may tend to be somewhat cumbersome in a catheter, and may have a need for special protection from the fluids it will encounter during use. Further, the process of transducing pressure to the desired electrical signal will carry some error which must be accounted for in the measurement circuitry.

Another solution to the problem used in the prior art is a catheter with an external inflation device for providing inflation fluid to the balloon. The external device carries a pressure gauge for monitoring inflation pressure in the balloon, from which data it is possible to determine the inflation level of the balloon in the manner described above.

SUMMARY OF THE INVENTION

The apparatus and method of this invention overcomes these difficulties by providing a novel method and apparatus for measuring the inflation of a balloon, in the form of at least one pair of electrodes mounted at spaced points in the interior of the balloon. Electrical conductors are connected to the electrodes and extend through and out of the catheter to be connected to an electrical measurement circuit. The balloon is inflated with an electrically conductive fluid having a relatively stable resistivity, and as the wall of the balloon expands the area containing the fluid changes, thus changing the value of the electrical parameters measured between the electrodes, in particular the resistance, according to the formula:

$$R = pL/A$$

where R is the resistance, p is the resistivity of the inflation fluid, L is the length of the balloon and A is the area within the balloon. In the preferred embodiment of this invention the resistance between the electrodes is monitored and, because the resistance measure is related to the inflation of the balloon, the result is presented to the physician in a form which gives him data on the inflation of the balloon.

BRIEF DESCRIPTION OF THE DRAWINGS

Other objects of the present invention and many of the attendant advantages of the present invention will be readily appreciated as they become better understood by reference to the following detailed description when considered in connection with the accompanying drawings, in which like reference numerals designate like parts throughout all figures.

DETAILED DESCRIPTION OF THE PREFERRED EMBODIMENT

Figure 1:
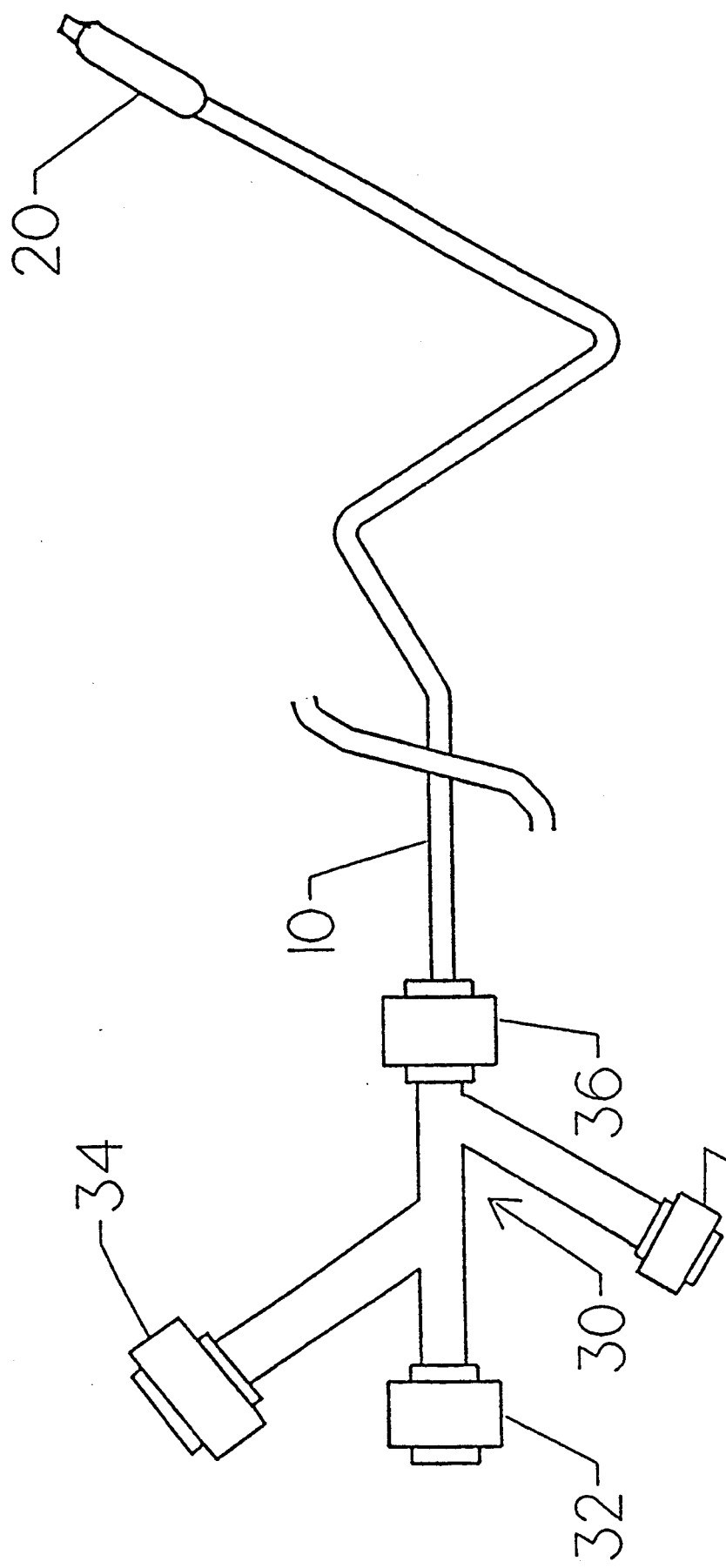
FIG. 1 is a view representative of a balloon catheter of one sort used in the apparatus of this invention.

FIG. 1 shows a dilation or balloon catheter shaft 10. Catheter shaft 10 is connected at its proximal end to a manifold 30 and at its distal end to a balloon 20. Catheter shaft 10 is connected to a port 36 of manifold 30. Also shown are ports 32 and 34 adapted to receive desired inputs such as a guide wire through port 32 to aid in the placement of balloon 20 within the body vessel, and an inflation fluid through port 34 to selectively expand balloon 20. Port 37 contains an electrical connector.

Figure 2:
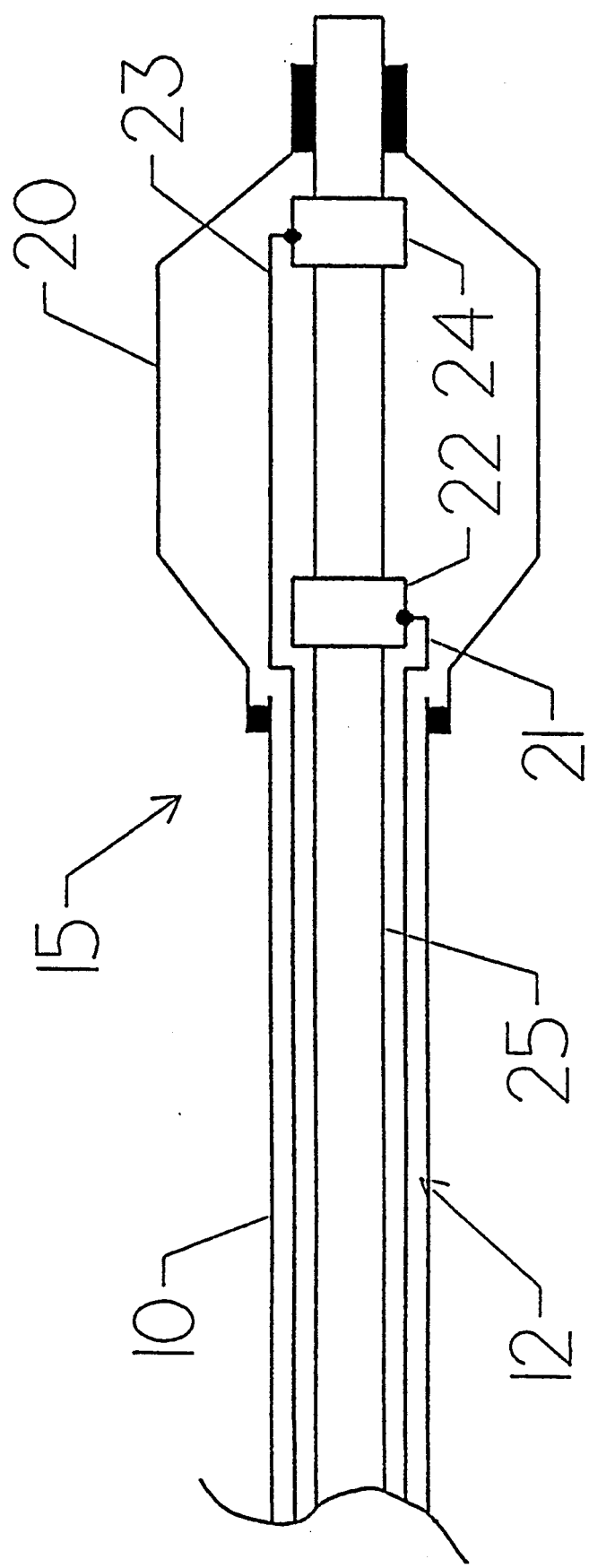
FIG. 2 is a partial cross-sectional view of a portion of the catheter of FIG. 1 showing a cut-away view representative of a balloon and the interior mountings of this invention as used in a conventional over-the-wire balloon catheter.

FIG. 2 is representative of a typical over-the-wire balloon catheter indicated at 15 and shown in cut-away form to reveal the interiors of the members which make up catheter 15. FIG. 2 shows a portion of catheter shaft 10 including a fluid lumen 12 defined therein. Also shown is representative balloon 20, with a shaft 25 passing through its interior. Balloon 20 is shown as sealed to catheter shaft 10 and inner shaft 25. It will be recognized that the constructions of shafts 10 and 25, and balloon 20 as shown in FIGS. 1 and 2 are merely representative of these elements of the various forms of balloon angioplasty catheters, and that this representative form of drawing has been selected for purposes of clarity in describing the present invention.

In FIG. 2 balloon 20 is shown having a pair of electrodes 22 and 24 mounted in spaced relation on inner shaft 25. In one embodiment shown in FIG. 2, electrode 22 and electrode 24 are mounted at opposite end of balloon 20. In this embodiment Of the invention inflation of balloon 20 by forcing fluid through lumen 12, will cause the walls of balloon 20 to expand thus changing the area within balloon 20 and therefore the resistance between electrodes 22 and 24, due to the fact that the inflation fluid is chosen to have a substantially constant resistivity. The cross-sectional area of balloon 20 between electrodes 22 and 24 is substantially constant. In other forms of angioplasty catheters, different mounting of the electrodes may be used. The essential requirement being that the electrodes be placed to sense the change in resistance as the internal area of the balloon is changed by insertion of an inflation fluid.

Continued reference to FIG. 2 shows that a pair of electrical conductors 21 and 23 extend through lumen 12 to be connected, respectively, to electrodes 22 and 24, Conductors 21 and 23 are adapted to be connected to an electrical circuit via port 37 of FIG. 1 for measuring the electrical parameters between electrodes 22 and 24, such as circuit 50 described below in the discussion of FIG. 3. It should be recognized that the number and placement of electrodes such as 22 and 24 may be altered and still lie within the scope of this invention; and that as the number of electrodes increases, so will the number of conductors increase. For example, as shown in FIG. 4, a plurality of electrodes 22A, 22B, and 22C, with associated conducts 21A, 21B, and 21C, and corresponding electrodes 24A, 24B, and 24C, with associated conductors 23A, 23B, and 23C may be located within balloon 20 for measuring electrical parameters within the electrodes to determine desired balloon 20 characteristics. Conductors 21A, 21B and 21C are routed along catheter shaft 10, as indicated by bus 21A, 21B, 21C, to be connected to an electrical circuit via port 37. Similarly, conductors 23A, 23B, 23C are routed along catheter shaft 10, as indicated by bus 23A, 23B and 23C to be connected to an electrical circuit via port 37.

Figure 3:
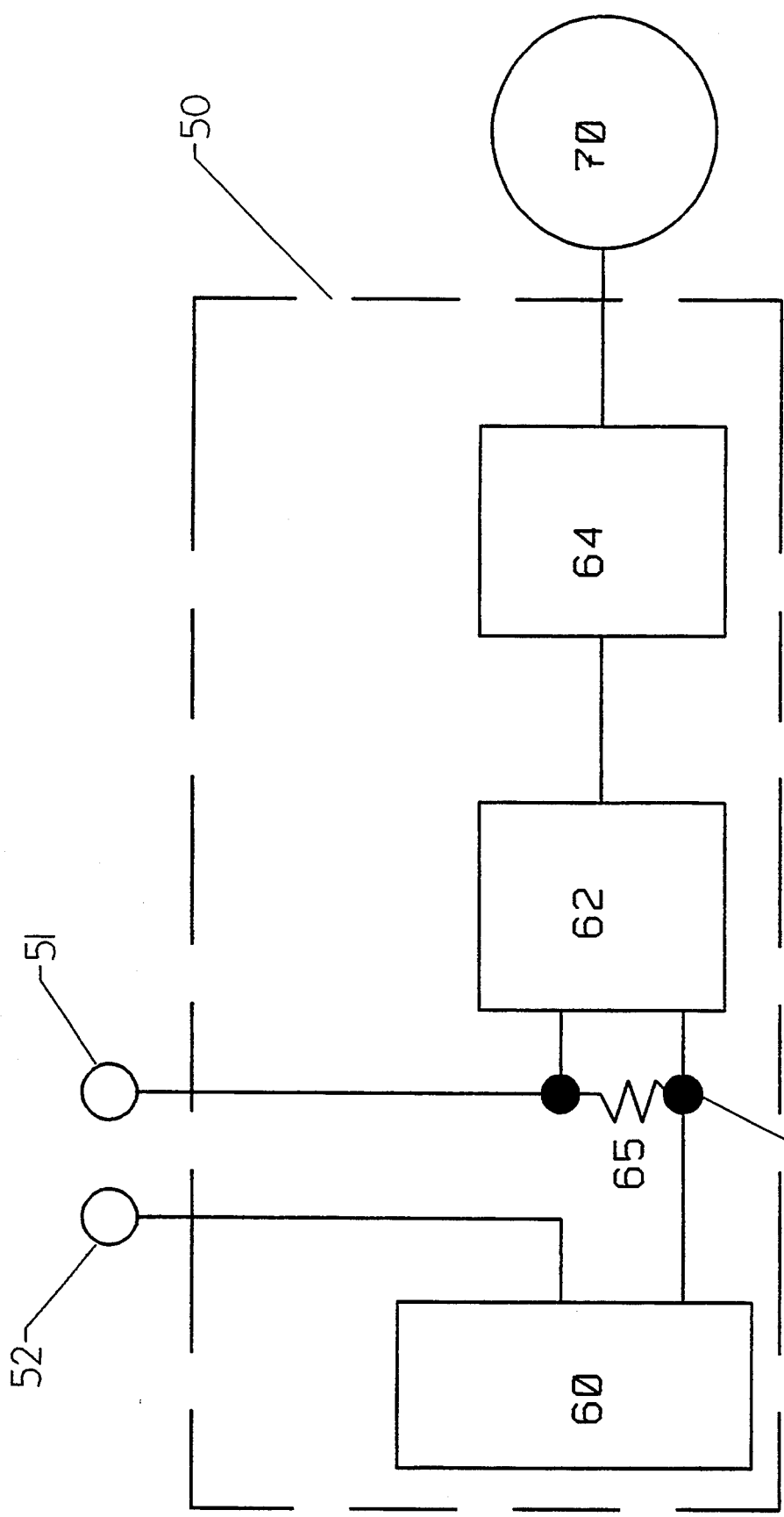
FIG. 3 is a schematic block diagram of the electrical measurement circuit of this invention.
Figure 4:
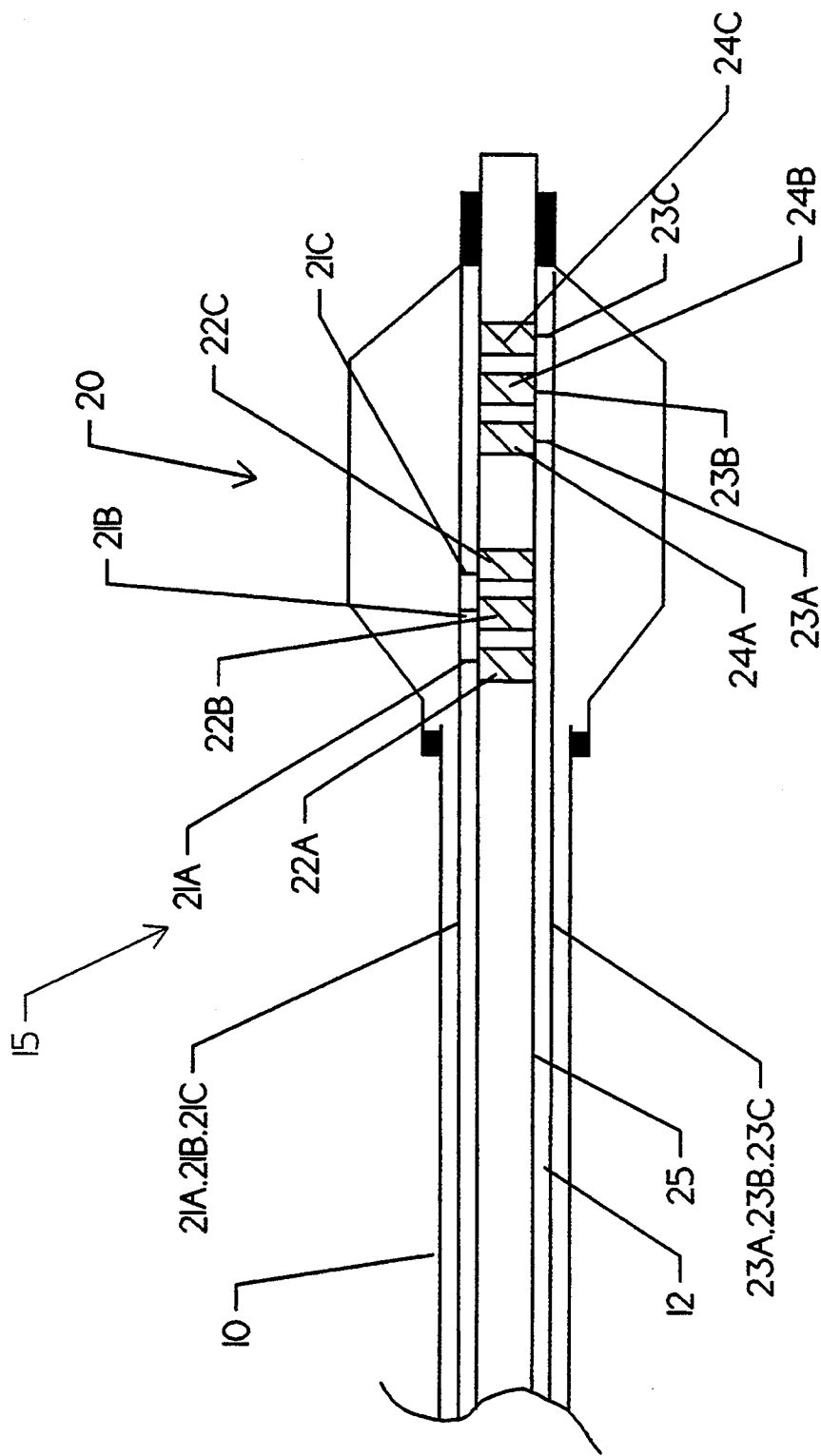

Referring to FIG. 3 there is shown a block diagram of an electrical measurement circuit 50 indicated in broken lines. A generator 60 is shown connected to a pair of terminals 53 and 52. Terminals 51a are in turn adapted to be connected, respectively, to conductors 21 and 23 of FIG. 2. Generator 60 may be, for example, a constant voltage generator. An amplifier 62 is also shown connected across current sampling resistor 65. Amplifier 62 is connected to a calculation circuit 64 for determining the value of the measured electrical parameter, and may be of any one of many known calculators, such as a minicomputer. Finally, the output of calculator 64 is connected to a display device 70, for displaying the desired data to the physician or other individual.

In normal operation of this preferred embodiment, when an electrically conductive fluid is passed through lumen 12 to inflate balloon 20, the area within balloon 20 varies. As the area varies, the current presented to electrodes 22 and 24 from generator 60 will meet with varying electrical resistance between them. This change in resistance is directly related to the amount of inflation of balloon 20, i.e. the movement of the wall of balloon 20 due to inflation is what causes the area to change. The electrical signal across electrodes 22 and 24 is felt through connectors 21 and 23 on terminals 51 and 52. Amplifier 62 receives and amplifies the signal on terminals 51 and 52, and passes the amplified signal to calculator 64 which determines the value of the electrical parameter being sensed, in this embodiment the resistance.

The calculated resistance is then passed to display unit 70, where it may be displayed along with a value representative of the inflation of balloon 20 which inflation value may be determined by knowing the relationship between the measured resistance and inflation of the type of balloon being used in the angioplasty procedure.

Generator 60 may also be a constant current generator.

Because the inflation fluid used in this invention will normally be presented to the body at a temperature lower than that of the body itself, the fluid must be chosen not only for its electrical properties in general, but should have a substantially constant resistivity at various temperatures. In the preferred embodiment described herein, the fluid used is a saline solution which has demonstrated the desired properties in testing.

Having thus described the preferred embodiments of the present invention, those of skill in the art will readily appreciate the other useful embodiments within the scope of the attached claims.

I claim:

1. Apparatus for measuring balloon inflation comprising:
   (a) an expandable balloon;
   (b) an electrically conductive inflation fluid;
   (c) at least first and second electrodes mounted in spaced relation within the balloon;
   (d) means for applying the electrically conductive inflation fluid within the balloon and for varying the internal area of the balloon; and
   (e) electrical connection means connected to the electrodes and adapted to connect the electrodes to an electrical circuit for measuring electrical parameters between the electrodes.

2. The apparatus of claim 1 including an electrical circuit for measuring electrical parameters connected by the electrical connection means to the electrodes.

3. The apparatus of claim 1 or 2 in which the electrical connection means comprises a pair of electrical conductors extending from the electrodes within the balloon to a point external to the balloon.

4. The apparatus of claim 1 in which the means for applying comprises a catheter connected to the balloon.

5. The apparatus of claim 1, 2 or 4 in which the electrically conductive inflation fluid comprises a saline solution.

6. The apparatus of claim 1 in which the electrically conductive inflation fluid has a substantially constant resistivity during temperature changes.

7. In a balloon catheter including a balloon having an interior wall and mounted at a distal end of the catheter and an inflation lumen connected to the interior of the balloon and extending at least to a proximal end of the catheter, and a balloon inflation measurement apparatus, the improvement comprising:
   a. an electrically conductive balloon inflation fluid;
   b. means connected to the proximal end of the inflation lumen for selectively providing the inflation fluid therethrough to the interior of the balloon;
   c. at least a pair of electrical electrodes within the balloon in spaced relation for monitoring changes in resistance as the inflation fluid varies the internal area of the balloon; and
   d. electrical connection means connected to the pair of electrodes and adapted to electrically connect an electrical measurement circuit to the pair of electrodes for measuring electrical parameters therebetween.

8. The balloon inflation measurement apparatus of claim 7 including a plurality of pairs of electrodes mounted within the balloon and in which the connection means adapted to electrically connecting the measurement circuit includes means adapted to electrically connect the measurement circuit to each pair of electrodes.

9. The balloon inflation measurement apparatus of claims 7 or 8 including an electrical measurement circuit connected to the electrical connection means for measuring the electrical parameters between each pair of electrodes.

10. The balloon inflation measurement apparatus of claim 9 in which the measurement circuit includes a constant current generator.

11. The balloon inflation measurement apparatus of claim 9 in which the measurement circuit includes a constant voltage generator.

12. The balloon inflation measurement apparatus of claim 9 in which the electrical parameter to be measured comprises electrical resistance.

13. The balloon inflation apparatus of claims 8 or 9 in which the electrically conductive balloon inflation fluid has a substantially constant resistivity during temperature changes.

14. The balloon inflation measurement apparatus of claim 9 in which the means for electrically connecting comprises at least one electrical conductor connected to each of the electrodes and extending through the inflation lumen for connection to the electrical measurement circuit.

15. The balloon inflation measurement apparatus of claim 8 in which the means for electrically connecting comprises an electrical conductor connected to each of the electrodes and extending through the inflation lumen and adapted to connect to an electrical measurement circuit.

16. The method of measuring balloon expansion in a balloon catheter comprising the steps of:
   a. mounting at least one pair of electrical electrodes in spaced relation within the balloon
   b. electrically connecting the electrodes to an electrical measurement circuit;
   c. inflating the balloon with an electrically conductive fluid to change the internal area of the balloon; and
   d. monitoring an electrical parameter between the pair of electrodes with the measurement circuit.

17. The method of claim 16 including the step of providing a constant current to the pair of electrodes.

18. The method of claim 16 including the step of providing a constant voltage to the pair of electrodes.

19. The method of claims 16, 17 or 18 including the step of monitoring the resistance between the pair of electrodes with the measurement circuit.

* * * * *